United States Patent
Wang

(10) Patent No.: US 10,605,755 B2
(45) Date of Patent: Mar. 31, 2020

(54) METHOD AND DEVICE FOR DETECTING CHARGED PARTICLES

(71) Applicant: Academia Sinica, Taipei (TW)

(72) Inventor: Yi-Sheng Wang, Taipei (TW)

(73) Assignee: Academia Sinica, Taipei (TW)

( * ) Notice: Subject to any disclaimer, the term of this patent is extended or adjusted under 35 U.S.C. 154(b) by 220 days.

(21) Appl. No.: 15/359,623

(22) Filed: Nov. 23, 2016

(65) Prior Publication Data

US 2017/0153195 A1    Jun. 1, 2017

Related U.S. Application Data

(60) Provisional application No. 62/261,317, filed on Dec. 1, 2015.

(51) Int. Cl.
| | |
|---|---|
| *G01N 27/02* | (2006.01) |
| *H01J 37/00* | (2006.01) |
| *G01N 1/00* | (2006.01) |
| *G01N 15/00* | (2006.01) |

(52) U.S. Cl.
CPC ............. *G01N 27/025* (2013.01); *G01N 1/00* (2013.01); *G01N 15/00* (2013.01); *H01J 37/00* (2013.01)

(58) Field of Classification Search
CPC ........ G01N 27/025; G01N 15/00; G01N 1/00; H01J 37/00

USPC ....... 324/600, 654, 425, 427, 500, 536, 678, 324/76.11, 76.32, 76.34–76.76, 87, 89

See application file for complete search history.

(56) References Cited

U.S. PATENT DOCUMENTS

| | | | |
|---|---|---|---|
| 2007/0228271 A1* | 10/2007 | Truche | H01J 49/142 250/288 |
| 2009/0190877 A1* | 7/2009 | Wang | G01N 21/554 385/12 |
| 2011/0186449 A1* | 8/2011 | Clochard | G01N 27/423 205/793 |
| 2012/0037802 A1* | 2/2012 | Kneedler | H01J 37/244 250/307 |
| 2013/0235357 A1* | 9/2013 | Delgado | G03F 7/70908 355/30 |
| 2016/0268113 A1* | 9/2016 | Brown | H01J 49/00 |

* cited by examiner

*Primary Examiner* — Vincent Q Nguyen
*Assistant Examiner* — Trung Nguyen

(57) ABSTRACT

The present invention relates to a device for detecting charged particles (e.g., ions). The device includes components arranged to neutralize or strip the charges of ions generated from a sample material, in which the charge stripping events produce signals that can be detected subsequently by a detector. A method for detecting charged particles generated from a sample material using the device is also provided.

18 Claims, 5 Drawing Sheets

METHOD AND DEVICE FOR DETECTING CHARGED PARTICLES

CROSS REFERENCES TO RELATED APPLICATIONS

This application claims priority from U.S. Provisional Patent Application No. 62/261,317, filed Dec. 1, 2015, which is incorporated herein by reference.

BACKGROUND OF THE INVENTION

1. Field of the Invention

The present disclosure relates in general, to the detection of charged particles. More specifically, the present disclosure relates to devices and methods for the detection of charged particles, in which the generation and the detection of the charged particles may respectively occur at the same or different phases.

2. Description of Related Art

Detecting ions is an essential process in sample identification. An ion detector is expected to provide high sensitivity, a fast response rate, and wide applicability, for numerous analytical methods examine ions produced from neutral analytes. Except for the optical sensors detecting specific ions exhibiting suitable optical activities, the choice of ion detection method in general varies with the is medium in which the ions of interest reside. In aqueous solutions, for example, ion detection can be achieved using electrical-conductivity, potentiometric, and polarographic detectors. Under vacuum and ambient conditions, ions can be collected using a metal electrode, also known as a Faraday electrode, and measured using an ampere meter. However, such detection methods are unable to provide the sensitivity and response time required for high-performance analysis. Although sensitive, accurate, and rapid ion analysis can be achieved using mass spectrometry (MS), the measurements cannot be conducted directly under ambient conditions mainly due to the working condition of high-gain ion detectors. In order to examine ions under ambient conditions or in an aqueous solution with a satisfactory signal quality, the development of a novel ion detector that functions effectively in harsh environments is necessary.

In view of the foregoing, there exists in this art a need of a much simplified design of a detector applicable to most types of spectrometers and could perform under liquid phase or ambient condition without losing its sensitivity or resolution of the detection.

BRIEF SUMMARY OF THE INVENTION

The present disclosure relates to methods and devices for detecting charged particles produced from a sample material.

Accordingly, it is the first aspect of the present disclosure to provide a device for detecting charged particles of a sample. The device comprises, a charge stripping means for stripping or neutralizing the charges of the charged particles generated from the sample thereby give rise to signals that correspond to the charge stripping or neutralizing events occurred therein; and a detection electrode for detecting the signals; wherein, the charge stripping means comprises at least one article made of a material capable of stripping or neutralizing the charges of the charged particles generated from the sample.

According to some embodiments, the material is selected from the group consisting of, a conductor, a semiconductor, an insulator and a combination thereof. Examples of the conductor include, but are not limited to, a metal, a conductive ceramic, a conductive glass, and a conductive polymer. Examples of the insulator include, but are not limited to, a ceramic, a glass, or a polymeric compound.

In one examples, the charge stripping means comprise an article made of metal. In other example, the charge stripping means comprise an article made of glass. In another examples, the charge stripping means comprise an article made of glass and metal, in which the metal is disposed as a layer on one side of the glass.

According to some optional embodiments, a hollow electrode is coupled to the charge stripping means, and help create an electric field that allows the generated ions to move toward the charge stripping means. In some examples, the hollow electrode consists of two washer-shaped electrodes, and the charge stripping means such as a nickel mesh, is sandwiched between the two washer-shaped electrodes.

According to further embodiments, the charge stripping means and the detection electrode may be positioned in the same or different environments that are of the same or different phases, such as liquid, air, or vacuum. In one example, the detection electrode is kept in air, while the charge stripping means is disposed in a liquid, such as hexane, heptane, toluene, and the like.

In some optional embodiments, the device of the present disclosure may further comprise a shield surrounding the detection electrode, so as to shield the detection electrode from ambient noise signals.

It is therefore the second aspect of the present disclosure to provide a method of detecting charged particles of a sample. The method comprises steps of, (a) generating charged particles from the sample;

(b) allowing the charged particles to collide with a charge stripping means positioned in a first electric field thereby give rise to signals that correspond to the charge stripping or neutralizing events; and (c) detecting the signals of the step (b) by a detection electrode positioned in a second electric field;

wherein, the first and second electric fields are configured to move the charged particles toward the charge stripping means and collide thereon, and prevent the charged particles from reaching the detection electrode; and the neutralizing means comprises at least one article made of a material capable of neutralizing or stripping the charges of the charged particles of the sample.

According to embodiments of the present disclosure, the charged particles are generated by ionizing the sample with a laser.

According to embodiments of the present disclosure, the first electric field is an accelerating filed having a strength of about 0 to 20,000 V/cm, while the second electric field is a retarding field having a strength of about 0 to 10,000 V/cm.

According to some embodiments, the charge stripping means is spaced apart from the sample and the detection electrode about 1 mm to 150 cm and about 0.1 mm to 10 cm, respectively.

According to some embodiments, the charge stripping means is made of a material selected from the group consisting of, a conductor, a semiconductor, an insulator and a combination thereof. Examples of the conductor include, but are not limited to, a metal, a conductive ceramic, a conductive glass, and a conductive polymer. Examples of the insulator include, but are not limited to, a ceramic, a glass, or a polymeric compound.

In one examples, the charge stripping means comprise an article made of metal. In other example, the charge stripping means comprise an article made of glass. In another examples, the charge stripping means comprise an article made of glass and metal, in which the metal is disposed as a layer on one side of the glass.

According to some optional embodiments, a hollow electrode is coupled to the charge stripping means, and help create an electric field that allows the generated ions to move toward the charge stripping means. In some examples, the hollow electrode consists of two washer-shaped electrodes, and the charge stripping means such as a nickel mesh, is sandwiched between the two washer-shaped electrodes.

According to further embodiments, the charge stripping means and the detection electrode may be positioned in the same or different environments that are is of the same or different phases, such as liquid, air or vacuum. In one example, the detection electrode is kept in air, while the charge stripping means is disposed in a liquid, such as hexane, heptane, toluene, and the like.

In some optional embodiments, the device of the present disclosure may further comprise a shield case surrounding the detection electrode, so as to reduce noise from ambient environment.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Figure 1A:
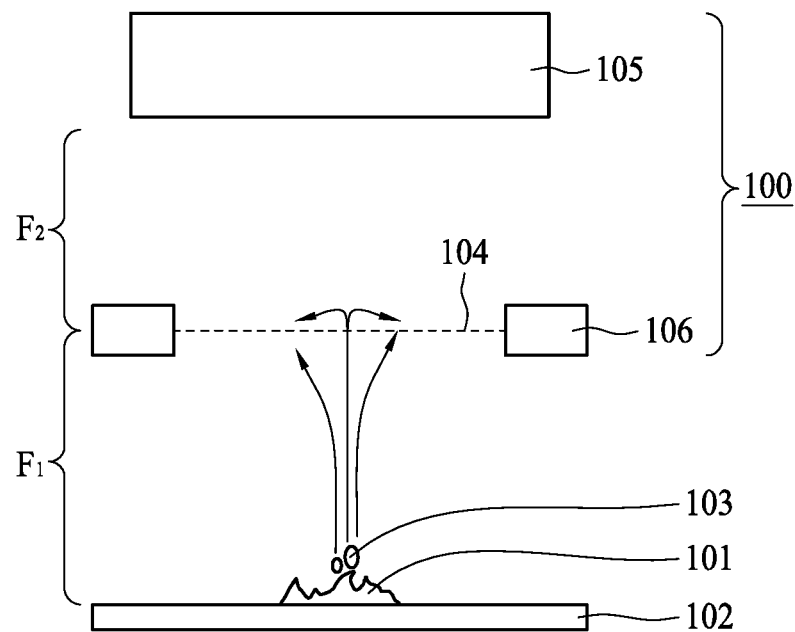
FIG. 1A is a schematic drawing illustrating the device 100 during a detection operation in accordance with one embodiment of the present disclosure.

Referring to FIG. 1A, which is a schematic drawing depicting the operation of a device 100 for detecting charged particles 103 produced from a sample material 101. The sample material 101 is first placed on the surface of a sample electrode 102, and ionized by any suitable means, such as a laser beam, so that charged particles (e.g., positive ions and negative ions) are generated. The newly produced charged particles, such as positive ions 103 of the sample material 101, are then detected by the device 100 of the present disclosure, which comprises a charge stripping means 104 and a detection electrode 105.

During operation, the sample electrode 102, the charge stripping means 104, and the detection electrode 105 are configured to create a first electric field $F_1$ between the sample electrode 102 and the charge stripping means 104, and a second electric field $F_2$ between the charge stripping means 104 and the detection electrode 105, in which the first and second electric fields ($F_1$, $F_2$) allow ions 103 to collide with the charge stripping means 104. Preferably, the $F_1$ is an accelerating field created between the sample electrode 102 and the charge stripping means 104 such that the newly generated ions 103 are attracted by, and move toward the charge stripping means 104 and eventually collide thereon, which results in the stripping of the charges carried by the ions 103, such as positive charges of the ions being stripped away. Further, the $F_2$ is a retarding field created between the charge stripping means 104 and the detection electrode 105 to prevent the ions 103 from reaching the detection electrode 105. The collision of ions 103 on the charge stripping means 104 neutralize the charged particles, in which each neutralization or stripping event corresponds to a signal that can be detected or measured by the detection electrode 105 positioned in the second electric field $F_2$.

Typically, the charge stripping means 104 of the present device 100 comprises at least one article made of a conductor, a semiconductor, an insulator, or a combination thereof. Examples of the conductor suitable for making the charge stripping means 104 include, but are not limited to, a metal (e.g., iron, nickel, copper, stainless steel, and the like); a conductive ceramic; a conductive polymer; and a conductive glass (e.g., a non-conductive glass having a layer of indium tin oxide (ITO) coated thereon). Examples of the insulator suitable for making the charge stripping means 104 include, but are not limited to, a ceramic, a glass and a polymeric compound (e.g., polyethylene (PE), polyvinylchloride (PVC), and the like). Further, whether the charge stripping means 104 is made of a conductor or an insulator, it preferably comprises a structure that allows the neutralization and/or stripping events occurred thereon to be detected by the neighboring detection electrode 105.

According to some embodiments, the charge stripping means 104 comprises an article made of metal, such as an article made of nickel (e.g., a nickel mesh). According to other embodiments, the charge stripping means 104 comprises an article made of metal and glass, in which the metal is disposed as a layer on one side of the glass. According to optional embodiments, charge stripping means 104 comprises an article made of a conductive glass, in which the conductive glass comprises a layer of indium tin oxide (ITO) coated thereon, so as to make the article conductive.

According to further embodiments, the charge stripping means 104 comprises two articles, arranged in sequence, the article made of metal (e.g., a nickel mesh), and the article made of glass, in which the glass article is positioned close to the detection electrode 105, and may or may not have a conductive layer (e.g., indium tin oxide (ITO)) coated thereon.

In the case when the charge stripping means 104 comprises an article made of any conductor described above or comprises a conductive layer coated thereon, a hollow electrode 106 may be coupled thereto; in which case, the hollow electrode 106 and the sample electrode 102 may be respectively biased to create the first electric field $F_1$ there between, which controls the trajectory of the ions 103 by attracting and moving them toward the charge stripping means 104, and eventually causing the ions 103 to collide on the surface of the charge stripping means 104 and give rise to the neutralization or stripping signal. Note that the trajectory of the ions 103 in $F_1$, or the orientation of the ions 103 traveling toward the electric means 104 is not limited, so long as they (e.g., ions 103) make it to the charge stripping means 104 and collide thereon to give rise to detectable signals. FIG. 1C is a schematic drawing depicting the ions 103a, 103b, 103c generated from the sample material 101 traveling from various directions in accordance with another embodiment of the present disclosure. For example, sample material 101 may be placed below or above the charge stripping means 104 thereby results in ions 103a and 103c traveling from below or above the charge stripping means 104. In other examples, sample material 101 may be placed adjacent to the charge stripping means 104 thereby results in ions 103b coming from a side direction and travel in a path that is relatively parallel to the charge stripping means 104.

Figure 1B:
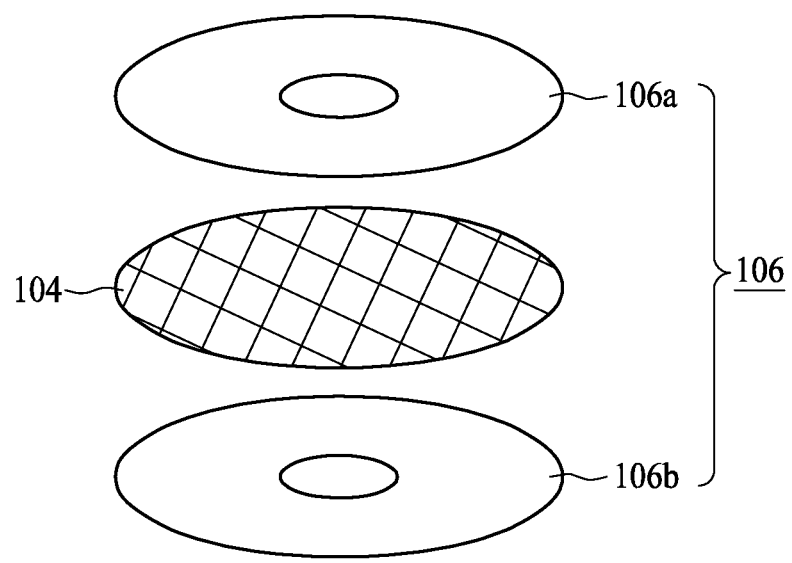
FIG. 1B is a schematic drawing illustrating the structure of a hollow electrode 106 in combination with the charge stripping means 104 in accordance with one embodiment of the present disclosure.
Figure 1C:
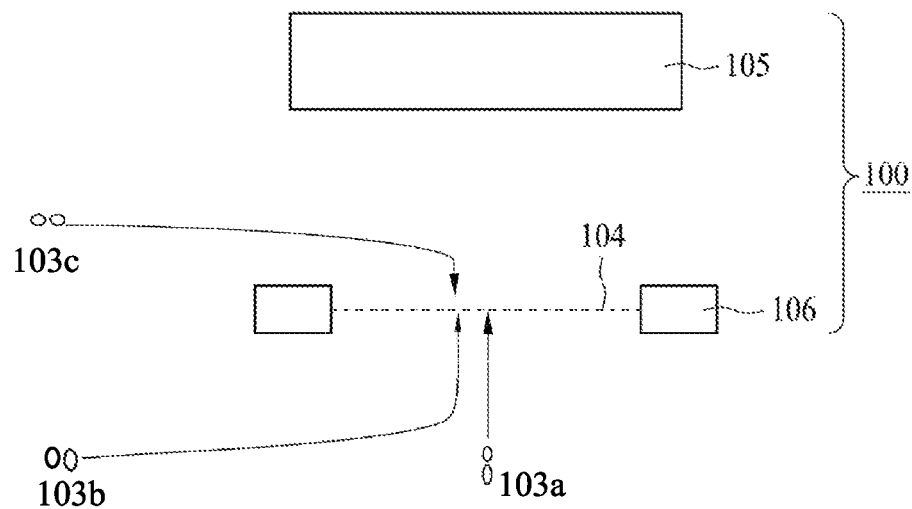
FIG. 1C is a schematic drawing illustrating the trajectory of ions 103a, 103b, and 103c respectively generated from sample materials disposed at various positions in relative to the charge stripping means 104, in accordance with one embodiment of the present disclosure.

Referring to FIG. 1B, in which an optional hollow electrode 106 is depicted and coupled to the charge stripping means 104. In this embodiment, an optional hollow electrode 106 consisting of two washer-shaped electrodes 106a and 106b, respectively having a central orifice, is depicted; and the charge stripping means 104 depicted as a metal mesh (e.g., nickel mesh), is sandwiched between the two washer-shaped electrodes 106a and 106b. In one optional embodiment, the sample electrode 102 and the hollow electrode 106 are respectively biased to create the first electric field $F_1$ that attracts ions 103 to move toward the charge stripping means 104 and eventually collide thereon.

The collision of ions 103 on the charge stripping means 104 results in the loss (e.g., stripping or neutralization) of the charges carried by the ions 103, and each neutralization or stripping event occurred at the charge stripping means 104 produces a signal that may be detected by a detection electrode 105 positioned in the second electric field $F_2$. In general, the first and second electric fields ($F_1$ and $F_2$) work cooperatively to control the trajectory of the ions 103 such that the ions 103 would collide on the surface of the charge stripping means 104 without reaching the detector 105. To this purpose, the charge stripping means 104 is preferably disposed at a distance about 1 mm to about 150 cm, more preferably about 1.5 mm to about 10 cm, and most preferably about 2 mm to about 1 cm, from the sample material 101 (or the sample electrode 102); whereas the charge stripping means 104 is disposed at a distance about 0.1 mm to about 10 cm, more preferably about 0.5 mm to about 5 cm, and most preferably about 1 mm to about 1 cm, from the detection electrode 105.

According to preferred embodiments, the first electric field $F_1$ is a field of acceleration designed to accelerate or preserve the movement of ions 103, and has a field strength from about 0 to 20,000 V/cm, more preferably from about 1,000 to 15,000 V/cm, most preferably, from about 5,000 to 10,000 V/cm; whereas the second electric field $F_2$ is a retarding field designed to prevent the ions 103 from reaching the detection electrode 105, and has a strength from about 0 to 10,000 V/cm, more preferably from about 10 to 5,000 V/cm, most preferably, from about 100 to 1,000 V/cm.

Optionally, a shield case (not depicted) may be used to shield the detection electrode 105 from the ambient noise, so that they do not interfere the operation of the detection electrode 105.

According to embodiments of the present disclosure, the charge stripping means 104 and the detection electrode 105 may be disposed in the same or different phases, such as liquid, air or vacuum. Examples of the liquid suitable for use in the present disclosure include, but are not limited to, hexane, heptane, toluene, and the like. In some embodiments, both the charge stripping means 104 and the detection electrode 105 are kept in the air. In other embodiments, both the charge stripping means 104 and the detection electrode 105 are placed in a vacuum environment. In further embodiments, the charge stripping means 104 is placed in a liquid (e.g., hexane); while the detection electrode 105 is kept in the air.

Figure 2:
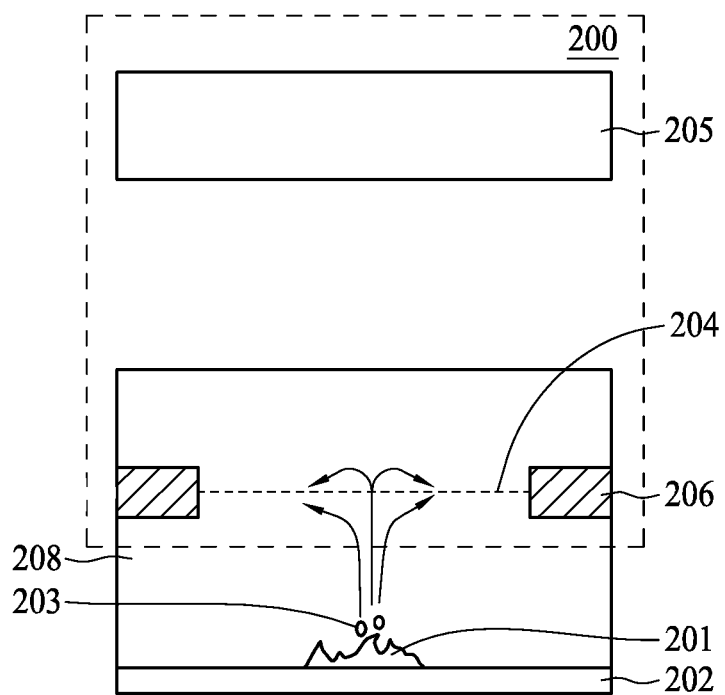
FIG. 2 illustrates a device 200 making a hetero-phase detection in accordance with one embodiment of the present disclosure.

FIG. 2 depicts another embodiment of the present disclosure, in which hetero-phase detection of the charged particles is made by use of a device 200. The components in device 200 are similar to those in device 100 as described above, except the sample electrode 202 and the charge stripping means 204 are placed in a liquid 208, whereas the detection electrode 205 is kept in air; further, an optional hollow electrode 206 coupled to the charge stripping means 204 is also depicted. While the detection electrode 205 is not in the same phase as that of the charge stripping means 204, however, the signals corresponding to the neutralization or stripping events occurred at the charge stripping means 204 can still be detected by the detection electrode 205. In fact, this hetero-phase detection is free-from direct interference of any residual charges or contaminants in the detection region (i.e., the region between the charge stripping means 204 and the detection electrode 205), therefore highest quality data may be gathered accordingly.

Figure 3:
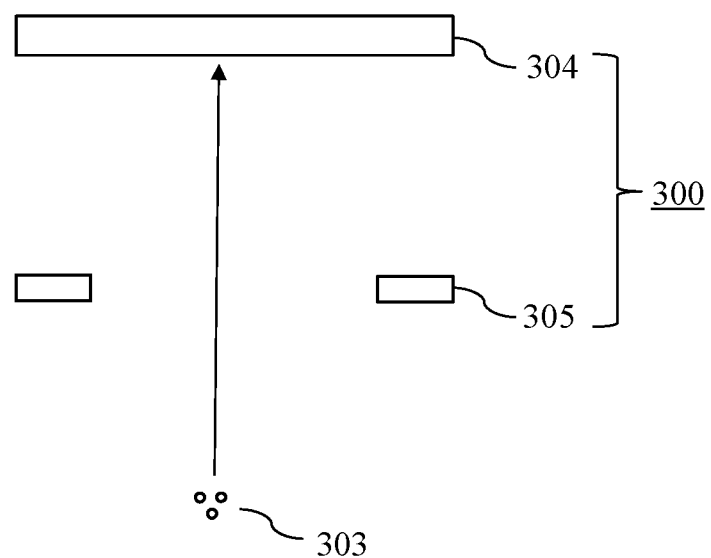
FIG. 3 is a schematic drawing illustrating the device 300 making a detection in accordance with one embodiment of the present disclosure.

FIG. 3 depicts another embodiment of the present disclosure, in which detection of the charged particles 303 is made by use of a device 300. The device 300 also include a charge stripping means 304 and a hollow detection electrode 306, with the arrangement being slightly different from the device 100, 200. In this embodiment, instead of placing the charge stripping means 304 in front of the hollow detection electrode 305 as the case in device 100, 200, the charge stripping means 304 is disposed after the hollow detection electrode 305, and is biased to an electric potential that attracts charged particles 303 to move toward the charge stripping means 304 without colliding on the hollow detection electrode 305, but on the charge stripping means 304. The collision of charged particles 303 on the charge stripping means 304 resulted in the neutralization of the charged particles 303, and each neutralization or charge stripping event would give rise to a signal that is detected or measured by the detection electrode 305.

The detector and detection method as described herein may be applied to various types of detection devices, including but is not limiting to, ion collectors, mass spectrometers, and ion mobility spectrometers.

For convenience, certain terms employed in the context of the present disclosure are collected here. Unless defined otherwise, all technical and scientific terms used herein have the same meaning as commonly understood by one of the ordinary skill in the art to which this invention belongs.

The singular forms "a", "an", and "the" are used herein to include plural referents unless the context clearly dictates otherwise.

The present invention will now be described more specifically with reference to the following embodiments, which are provided for the purpose of demonstration rather than limitation.

EXAMPLES

The following describe an example of the present device that was used to conduct the experiments.

Briefly, a sample electrode, a hollow electrode, and a detection electrode were positioned horizontally, with typically 3 mm between the sample and the hollow electrode and 5 mm between the hollow and the detection electrode. The sample electrode was a rectangular plate fixed on a motorized x-y stage. The hollow electrode consisted of two identical 0.5 mm thick washer-shaped electrodes (5 mm i.d.×20 mm o.d.) that were stacked together. A nickel mesh (BM0020-03N, Industrial Netting, Minneapolis, Minn.) was fixed between them to cover the central orifice. The mesh was composed of 32 μm thick wires with an aperture width of 1238 μm. The detection electrode was a 2 mm thick, 16 mm o.d. cylindrical electrode with a 4 mm i.d. central orifice. Except for the sensing surface (bottom), the detection electrode was enclosed in a stainless steel housing to minimize ambient electronic noise. The detection electrode was connected to a fast current preamplifier (DLPCA-200, FEMTO Messtechnik GmbH, Berlin, Germany), and the output signal of the preamplifier was monitored by a digital oscilloscope (RTO, Rohde & Schwarz Taiwan Ltd., Taipei, Taiwan). To detect positive ions, the sample and the hollow electrode were biased at +4000 V and −500 V, respectively, corresponding to an acceleration field of 15000 V/cm. The hollow and the detection electrode defined a retarding field of 1000 V/cm for positive ions.

The analytes on the sample plate were ionized using laser desorption ionization (LDI) method. A frequency-tripled Nd:YAG laser beam (355 nm, LS-2134 UTF, Lotis TII Ltd., Minsk, Belarus) was used in this example. The laser beam examined the sample perpendicularly after passing through the central orifice of the detection and the hollow electrodes. The laser beam was focused by a 125 mm fused silica plano-convex lens to a spot approximately 139 μm in diameter on the sample surface. The laser energy was regulated from 2 to 400 μJ by using a half-wave plate system (Attenuator 355 nm, Lotis TII Ltd., Minsk, Belarus). Each spectrum was obtained using 20 laser shots.

To analyze ions in the gas phase, the entire device was kept in an ambient environment. To analyze ions in the liquid phase, a non-conductive liquid was used to sustain the electric potential of the sample and hollow electrodes. The liquid measurement was operated in a single-phase mode or hetero-phase mode. In the single-phase mode, all electrodes were immersed in liquid; in the hetero-phase mode, the detection electrode was kept in air, while the other electrodes were immersed in liquid. To ensure the detected signal was entirely due to the charge induction, a cover slip (φ=18 mm, thickness=0.15 mm, Paul Marienfeld GmbH & Co. K G, Lauda-Königshofen, Germany) was used in confirmation tests to block the detection electrode to prevent any direct contact with particles (results not shown). The observed spectra were obtained without the additional cover slip unless mentioned otherwise. The gain and bandwidth settings of the preamplifier were $10^8$ and 200 kHz, respectively, for detecting ions in air. The settings were $10^9$ and 1 kHz, respectively, for detecting ions in non-conductive liquids.

Hexane was used throughout the experiments as a non-conductive liquid. The samples include cesium iodine (CsI), 2,5-dihydroxybenzoic acid (DHB), and Ti nanoparticles (30-50 nm, UniRegion Bio-Tech, Hsinchu, Taiwan). The CsI and DHB were dissolved in distilled, deionized water before preparation, whereas the Ti nanoparticles were suspended in distilled, deionized water through vortexing and preparation before re-precipitation. The amount of CsI deposited on the sample electrode was approximately 5 mg, and the amounts of DHB and Ti deposited were approximately 2.5 mg each. All chemicals were purchased commercially and were used without further purification. Results are summarized in FIGS. 4 and 5.

Figure 4:
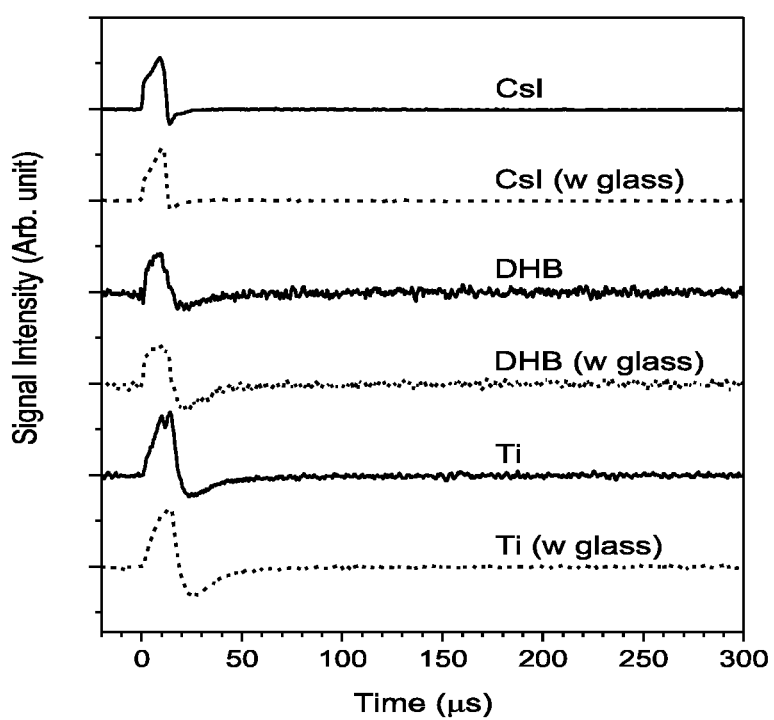
FIG. 4 are traces of the signals arise from neutralization or stripping of the charged particles from various samples detected by the present device in accordance with one embodiment of the present disclosure.

FIG. 4 are traces of the induction signals of CsI, DHB and Ti nanoparticles obtained in the air, with or without a cover slip installed in front of the detection electrode. As the traces presented in FIG. 4, the bottom of the signal was used to report the time-of-arrival (TOA) in the present example. The TOA of the CsI, DHB, and Ti as illustrated in FIG. 4 peaked at 14.0, 17.6, and 23.6 μs, respectively.

The hetero-phase experiments were conducted by immersing the sample and the hollow electrode in hexane, while keeping the detection electrode in air. The level of hexane was maintained at 2-4 mm above the hollow electrode to ensure that the trajectory of ions did not pass through the liquid-air boundary. Under such experimental conditions, the movement of the motorized stage was kept slow to prevent severe vibrations in the liquid, which could interfere with the trajectory of ions and hence changed the TOA. The motorized state was inactivated during induction signal detection to avoid electronic noise detection. Results are illustrated in FIG. 5.

Figure 5:
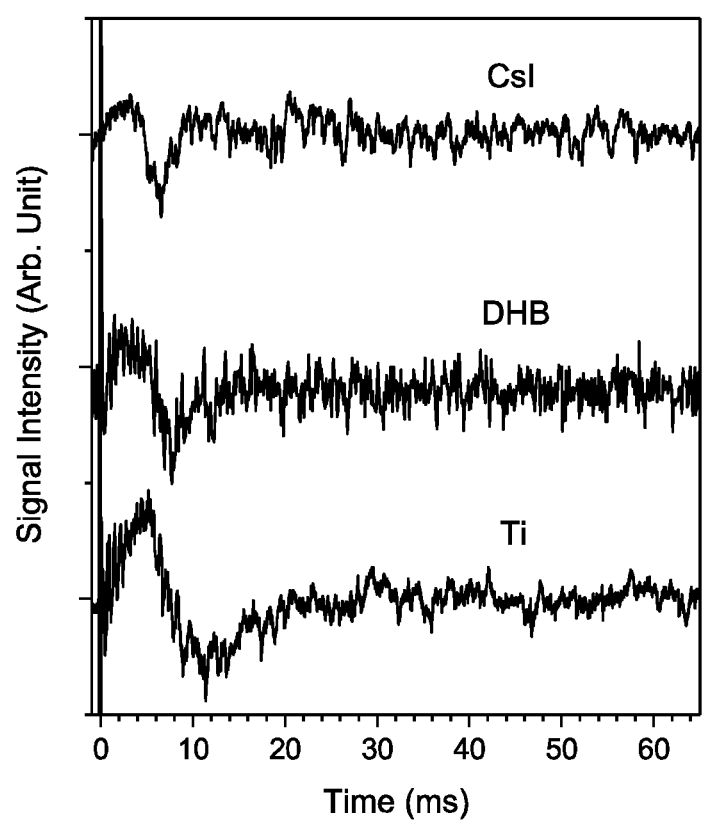
FIG. 5 are traces of the signals arising from neutralizing or stripping of the charged particles from various samples detected by the present device in accordance with another embodiment of the present disclosure.

FIG. 5 are traces depicting the signals of CsI, DHB, and Ti in hexane. Due to the large drag of hexane, the spectra exhibited features appearing several ms after laser excitation. The main feature of the three samples populated within 30 ms. The major TOAs for CsI, DHB, and Ti obtained in hexane were roughly 6.7±1.1, 7.5±0.7, and 11.5±0.6 ms, respectively. Such TOA values were roughly 420-490 times higher than those in the air.

Taken together, the experimental result suggests that detecting the charge stripping or neutralization by the present device and/or method is highly efficient, even in the liquid phase.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A device for detecting charged particles of a sample comprising,
    a charge stripping means for stripping the charges of the charged particles generated from the sample, in which each charge stripping event produces a signal; and
    a detection electrode for detecting the signals;

wherein,
the charge stripping means and the detection electrode are configured to create an electric field for preventing the charged particles from reaching the detection electrode; and
the charge stripping means comprises at least one article made of a material capable of stripping the charges of the charged particles generated from the sample.

2. The device of claim 1, wherein the material is selected from the group consisting of, a conductor, a semiconductor, an insulator and a combination thereof.

3. The device of claim 2, wherein the conductor is a metal, a conductive ceramic, a conductive glass or a conductive polymer; and the insulator is a ceramic, a glass, or a polymeric compound.

4. The device of claim 3, wherein the charge stripping means comprise an article made of glass and metal, in which the metal is disposed as a layer on one side of the glass.

5. The device of claim 2, wherein the charge stripping means and the detection electrode are respectively disposed at different phases.

6. The device of claim 5, wherein the phase is liquid, air or vacuum.

7. The device of claim 6, wherein the liquid is any of hexane, heptane, or toluene.

8. The device of claim 6, wherein the charge stripping means is placed in the liquid, while the detection electrode is kept in the air.

9. A method for detecting charged particles of a sample, comprising,
(a) generating charged particles from the sample;
(b) generating a first electric field with a charge stripping means to allow the charged particles to collide with the charge stripping means, in which the collision results in charges being stripped from the charged particles and the generation of signals that correspond to the charge stripping events; and
(c) detecting the signals of the step (b) by a detection electrode, which is positioned in a second electric field to prevent the charged particles from reaching the detection electrode;
wherein,
the first and second electric fields are configured to, move the charged particles toward the charged stripping means and collide thereon, and prevent them from reaching the detection electrode.

10. The method of claim 9, wherein the first electric field is an accelerating field having a strength of about 0 to 20,000 V/cm, and the second electric field is a retarding field having a strength of about 500 to 1,000 V/cm.

11. The method of claim 10, wherein the charge stripping means is spaced apart from the sample and the detection electrode about 1 mm to 150 cm and about 0.1 mm to 10 cm, respectively.

12. The method of claim 9, wherein the charge stripping means is made from a material selected from the group consisting of, a conductor, a semiconductor, an insulator and a combination thereof.

13. The method of claim 12, wherein the conductor is a metal, a conductive ceramic, a conductive glass or a conductive polymer; and the insulator is a ceramic, a glass, or a polymeric compound.

14. The method of claim 13, wherein the charge stripping means comprise an article made of glass and metal, in which the metal is disposed as a layer on one side of the glass.

15. The method of claim 9, wherein the charge stripping means and the detection electrode are respectively disposed at different phases.

16. The device of claim 15, the phase is liquid, air or vacuum.

17. The method of claim 16, wherein the liquid is any of hexane, heptane, or toluene.

18. The method of claim 16, wherein the charge stripping means is placed in the liquid, while the detection electrode is kept in the air.

* * * * *